United States Patent [19]

Schmid

[11] 4,273,000
[45] Jun. 16, 1981

[54] DRIVE MECHANISM FOR A DRUM

[75] Inventor: Alfred Schmid, Schöfflisdorf, Switzerland

[73] Assignee: Bucher-Guyer AG, Zürich, Switzerland

[21] Appl. No.: 932,926

[22] Filed: Aug. 11, 1978

[30] Foreign Application Priority Data

Aug. 24, 1977 [DE] Fed. Rep. of Germany ....... 2738172

[51] Int. Cl.³ .................... F16H 13/02; B28C 5/18
[52] U.S. Cl. .................................. 74/206; 34/108; 74/209; 366/54; 366/62; 366/63
[58] Field of Search ............... 74/202, 203, 215, 206, 74/208, 209; 105/265; 241/176, 178; 69/30; 34/108; 432/103; 366/54, 56, 57, 58, 59, 60, 62, 63, 233

[56] References Cited

U.S. PATENT DOCUMENTS

| 584,521 | 6/1897 | Rich | 74/206 |
|---|---|---|---|
| 1,665,902 | 4/1928 | Bastian | 74/215 |
| 2,570,082 | 10/1951 | Traylor, Jr. | 74/206 |
| 2,576,210 | 11/1951 | Bojner | 74/206 X |
| 2,726,047 | 12/1955 | Treshow | 74/209 X |
| 3,016,232 | 1/1962 | Domenighetti | 366/63 |
| 3,033,057 | 5/1962 | Gray | 432/103 X |
| 3,474,647 | 10/1969 | Dandliker | 69/30 |
| 3,487,705 | 1/1970 | Fox | 74/209 |
| 3,795,121 | 3/1974 | Cressman | 69/30 |

FOREIGN PATENT DOCUMENTS

| 17431 | 9/1893 | Fed. Rep. of Germany | 74/206 |
|---|---|---|---|
| 583002 | 8/1933 | Fed. Rep. of Germany | 241/176 |
| 1036595 | 8/1958 | Fed. Rep. of Germany | 74/209 |
| 1078379 | 3/1960 | Fed. Rep. of Germany | 366/233 |
| 1177448 | 9/1964 | Fed. Rep. of Germany | 74/202 |
| 2228987 | 12/1974 | Fed. Rep. of Germany | 74/202 |
| 1095216 | 5/1955 | France | 74/215 |
| 1352615 | 1/1964 | France | 74/202 |
| 1395356 | 3/1965 | France | 366/233 |
| 421720 | 5/1947 | Italy | 74/209 |
| 169395 | 11/1959 | Sweden | 241/178 |
| 313213 | 6/1929 | United Kingdom | 74/206 |
| 887188 | 1/1962 | United Kingdom | 74/206 |

Primary Examiner—Leslie Braun
Attorney, Agent, or Firm—Ernest F. Marmorek

[57] ABSTRACT

A relatively large drum which is supported by rotation about a horizontal axis of rotation is driven by a drive mechanism. The above mechanism includes an energizable rotor that is resiliently and rotatably supported, and in frictional contact with the circumference of the drum, so as to rotate the drum when energized.

11 Claims, 3 Drawing Figures

DRIVE MECHANISM FOR A DRUM

BACKGROUND OF THE INVENTION

There are known cylindrical drums, particularly drums adapted to contain liquids in fermentation, or for juice extraction, which drums are horizontally supported on their respective side surfaces by two axles centrally extending therefrom, the axles being rotatably supported. One axle serves as a drive shaft and includes a relatively large drive wheel or rotor, which is coupled to a gear train to reduce the number of revolutions compared to the number of revolutions of a drive motor, to which the drive wheel is coupled. Gear trains which have been used include gear wheels, such as spur gears, bevelled gears, or worm gears, as well as drive means using tension, such as bands, belts or various types of chains. Hydraulic drive means are also known for this purpose.

Drums of this type, capable of containing up to 60 tons, do, however, present drive problems, which are primarily due to the fact that these drums are centrally driven. This in turn requires gear trains of relatively large dimensions, which are costly and relatively complicated, in order to obtain the required reduction in the number of revolutions of the drive motor. Furthermore, the larger the diameter of the drum, the smaller must be the number of revolutions of the drum. Gear trains suitable for driving such drums then become so expensive, that it is no longer economically worthwhile to further enlarge the drum. In practice therefore, a plurality of drums are used for this purpose.

SUMMARY OF THE INVENTION

One of the principal objects of the present invention is therefore to devise drive means, which are constructed to achieve the desired relatively low number of revolutions, particularly for relatively large drums, and which are simply constructed, and therefore relatively inexpensive.

This object is attained in drive arrangements of the previously described kind, by providing a drive mechanism for rotating a relatively large revolvable drum, which includes a support, the drum being supported for rotation about its axis of rotation from the support, and drive means, including an energizable rotor, resiliently and rotatably supported on the support, and in frictional contact with the circumference of the drum, so as to be operable for rotating the drum when energized.

This renders it unnecessary to provide a multiplicity of reduction gears for relatively large drums, as the circumference of the drum itself is integrally involved in the reduction of the number of revolutions of the drive motor. It is alternately possible to consider the peripheral velocity of the drum as dependent on the peripheral velocity of the driver rotor, the peripheral velocities being equal to one another, so that the correct number of revolutions is always obtained independently of the diameter of the drum. Thus, the gear train will not be more complicated or more costly, as the size of the drum increases.

In a preferred implementation, the drive means further include an energizing wheel rotatably supported on the support about its axis of rotation on one side of a plane passing through the axes, and in driving connection with the energizable rotor, for energizing it to revolve in a predetermined rotational direction, so as to drive the drum in a rotational direction opposite to the predetermined rotational direction. In one version of the invention, both the rotor and the energizing wheel are formed as a roller. Resilient means are provided for urging the roller into frictional contact with both the energizing wheel, and the drum circumference.

The energizing wheel is preferably centrally disposed on the support, the force of the resilient spring effecting the frictional engagement between the drum and the rotor, so that any slip and the maximal torque is dependent thereon. The force of the spring is further enhanced by the inlet effect resulting from an operative combination of the drum, and the rotor.

In order to drive the drum in both directions of rotation equally, in a further advantageous implementation, the drive means further comprise a second energizable rotor in operative contact with the drum, and resiliently and rotatably supported on the support about an axis of rotation located on the other side of the plane. It will thus be seen that one rotor is disposed on the inlet side, and the other on the outlet side of the drive mechanism.

It is advantageous if the first energizable rotor includes a first shaft, and the energizable wheel includes a second shaft, and if a first elongated guide is provided, which is pivotably supported with one end thereof on the first shaft, and a second elongated guide is provided which is pivotably supported with one end thereof on the second shaft, the other ends of the guide being pivotably connected to one another, and if resilient means are included supporting a portion of the second guide at a position spaced apart from the second shaft, thereby pressing the energizable rotor into frictional contact with the drum circumference and with the energizing wheel. It is further advantageous if the guides form an acute angle with one another; it will readily be seen that the spring exerts a pressure on the drum. In practice, there is provided on each side of the energizing wheel a rotor, each rotor having a pair of guides. The guides also serve to align the shaft or shafts of the rotors.

In order to insure as large a frictional surface between the drum and the rotor or rotors, as well as between the rotor and the energizing wheel, it is advantageous if the rotor includes rollers.

It is particularly advantageous if the energizable rotor includes a plurality of hubs of prearranged hub diameters, a frictional ring of yieldably resilient material and of a predetermined ring diameter disposed on each hub, and at least one spacer of a predetermined diameter separating two adjacent hubs from one another, wherein the predetermined diameter is larger than the hub diameter, but less than the ring diameter. If the friction rings are worn, then the spacers insure that the hubs are not damaged. The friction rings further serve to visibly show that a maximum wear has taken place. It is further advantageous if each friction ring is tapered in a radially outward direction, so as to converge.

It is further advantageous if each rotor has a predetermined width, and the drum has a portion of increased thickness in the region of the rotor width.

BRIEF DESCRIPTION OF THE DRAWINGS

For a fuller understanding of the nature and objects of the invention, reference should be had to the following detailed description, taken in connection with the accompanying drawings in which.

DESCRIPTION OF THE PREFERRED EMBODIMENTS

Figure 1:
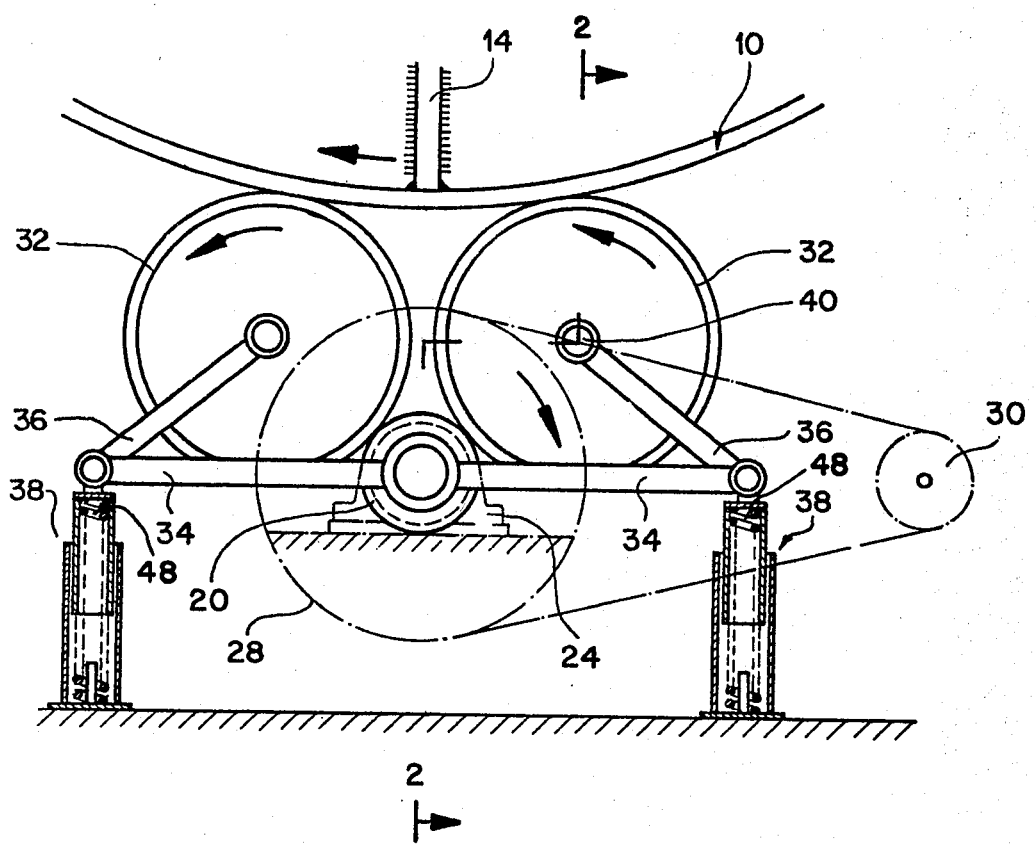
FIG. 1 shows an elevational view of one version of the present invention.
Figure 2:
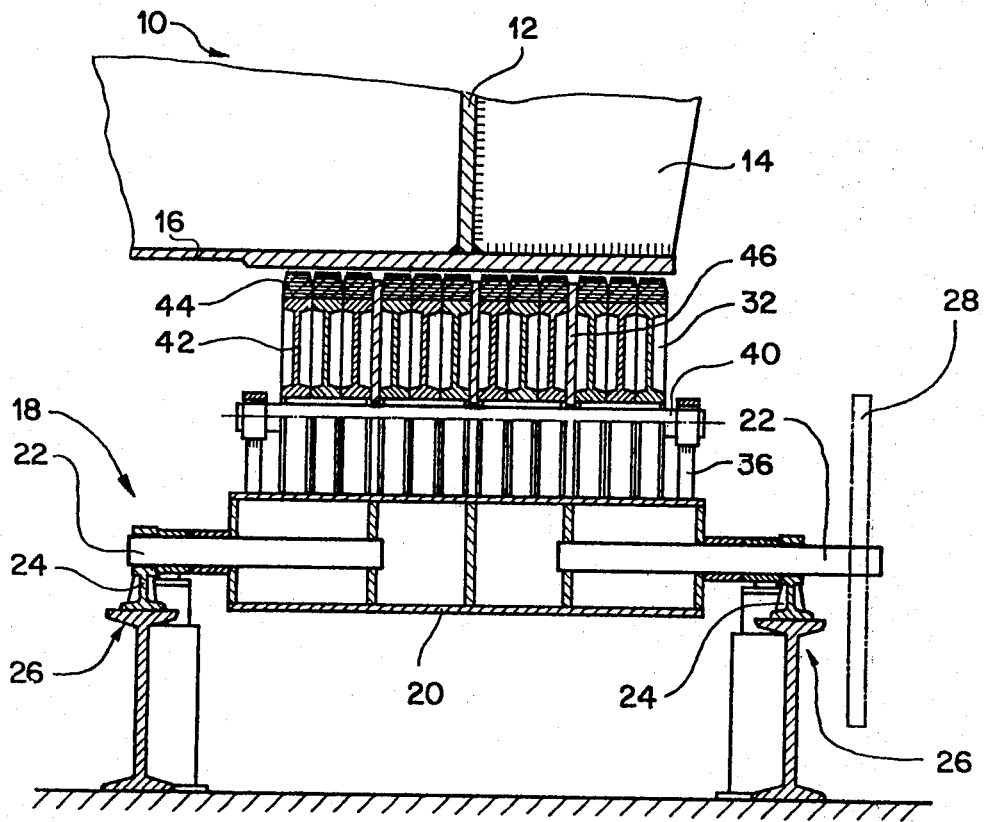
FIG. 2 is a section along the line 2—2 of FIG. 1.
Figure 3:
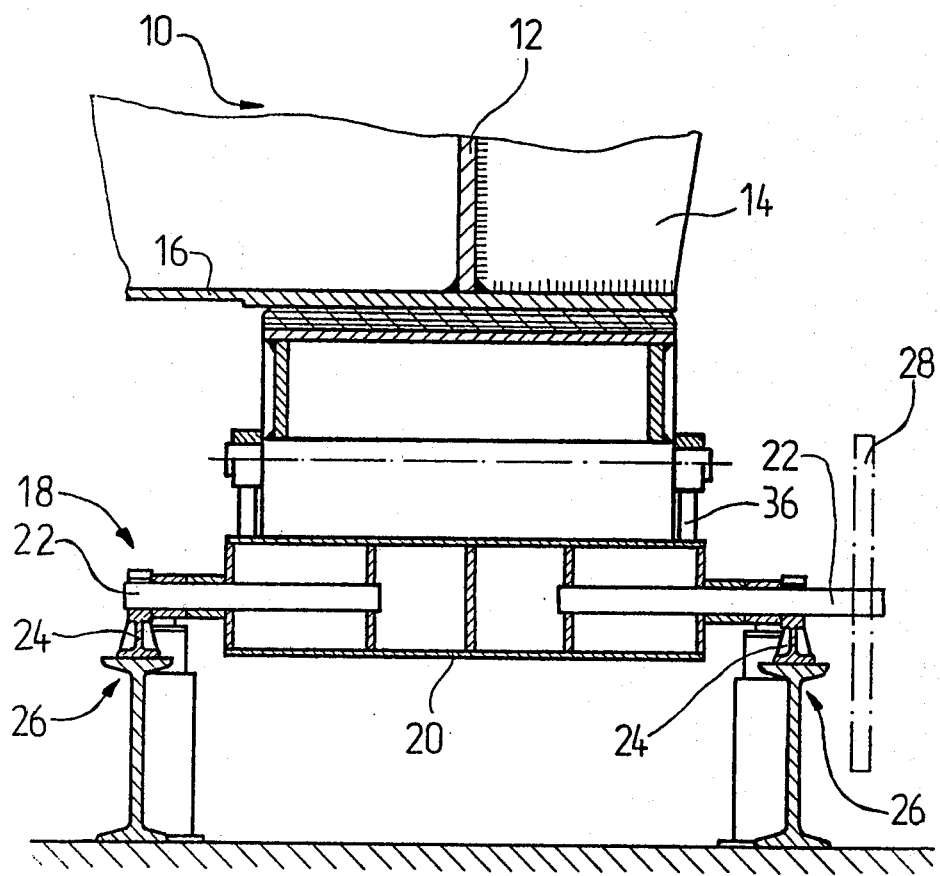
FIG. 3 is a section of an alternate embodiment of the invention along the lines 2—2 of FIG. 1.

In carrying the invention into effect, in a preferred implementation example, according to FIGS. 1 and 2, a cylindrical drum 10 adapted to contain, for example, a liquid in fermentation, is supported for rotating about a horizontal axis of rotation. Only a fragment of the drum 10 is shown in the drawings. Both end walls 12 (only one end wall 12 being shown in FIG. 2), are set back from the very end of the drum, each end wall including a (non-illustrated) supporting axle that projects from its center; these axles are rotatably supported in (non-illustrated) bearings. The supporting axles are connected through ribs 14 (FIG. 1) to the interior of the shell 16 of the drum 10, the drum 10 having a circumference zone of increased diameter within the region of the drive means, which are generally indicated at 18.

The drive means 18 include an energizing wheel 20, which has an axis disposed in parallel to the axis of rotation of the drum 10, the energizing wheel 20, having axles 22 projecting from each of its sides, which are rotatably supported in bearings 24. The bearings 24 in turn are set on supports 26, the supports 26 resting on the floor. One axle 22 has a sprocket wheel secured to its outer end. A chain interconnects the sprocket wheel 26 with a pinion 30 of a drive motor.

Two rotors 32 are provided, which have their rotation axes disposed also parallel to the axis of rotation of the drum 10. The rotors 32 are disposed symmetrically between the energizing wheel 20 and the drum 10, about a plane intersecting the axis of rotation of the drum, and the axis of rotation of the energizing wheel 20. The rotors 32 are in rolling contact with the shell 16 of the drum 10, as well as with the energizing wheel 20.

The axial length of the rotors 32, as shown in FIG. 2, is somewhat smaller than the length of the energizing wheel 20. Each rotor 32 includes a pair of elongated guides on each side thereof, including a guide 34 and a guide 36. Each elongated guide 34 is rotatably supported on an end thereof on a corresponding axle 22 of the energizing wheel 20, and is pivotably supported with its other end approximately at the same height as the axle 22 on a support leg 38, so that it can pivot horizontally. Each elongated guide 36 is also pivotably supported with one end about a horizontal axis on the support leg 38, and is rotatably connected with its other end to a shaft 40 of a corresponding rotor 32. The elongated guides 34 and 36 form an acute angle with one another, the ratio of the length of the elongated guides 34 and 36 being, in the example shown, approximately 3:2, while the angle formed or subtended between the guides 34 and 36 is, in the example shown, approximately 40 degrees. The ratio of the diameter of the rotors 32 to the diameter of the energizing wheel 20 is, in the example shown, approximately 4:1, while the ratio of the diameter of the drum to the diameter of the rotor is, according to the example shown, approximately 5:1.

On the shaft 40 of the rotor 32, there are mounted for rotation with the shaft a plurality of groups of hubs 42, each group of hubs 42 including, in the example shown, three hubs 42, a rubber ring 44 being disposed on the outer periphery of each hub 42, the rubber ring 44 having a trapezoidal cross-section tapered in a radially outward converging manner. The groups of steel hubs 42, as well as the corresponding rubber rings 44, are separated from one another by spacers 46, the outer diameter of which is smaller than the outer diameter of each rubber ring 44, but larger than the outer diameter of each hub 42. When the rubber rings 44 wear in the course of time, then the shell 16 of the drum 12, and the energizing wheel 20, do not come in contact with the hubs 42, but with the spacers 36, so that the hubs 42 are protected. Furthermore, with the aid of the spacers 46, a critical degree of wear can be easily ascertained, particularly if the mechanism is so arranged, that upon the rubber rings 44 being worn down up to the diameter of the spacers 46, an entirely smooth surface appears, instead of the corrugated surface usually visible on each rotor 32.

A first reduction in the transmission ratio from the non-illustrated energizing motor is obtained through the pinion 30 and the sprocket wheel 28. A second reduction is obtained as a result of the much smaller diameter of the energizing wheel 20, compared to that of the sprocket wheel 28. A third reduction is due to the much larger diameter of the rotor 32, compared to that of the energizing wheel 20. A final transmission ratio reduction occurs due to the much larger diameter of the drum 10, compared to that of the rotor 32.

The drive means illustrated in FIGS. 1 and 2, could also, alternatively, be provided with only a single rotor 32. A single rotor would then have to be provided on the right side of the energizing wheel 20, as shown in FIG. 1, namely on its inlet side. The rotor 32 on the right side of FIG. 1 transmits a larger torque to the drum 10 than the rotor 32 on the left side of FIG. 1, in view of the larger frictional force exerted thereon. The rotor 32 on the left side of FIG. 1, which is disposed on the outlet side, contributes much less to the drive of the drum 10, as can be ascertained from a force diagram. The rotor 32 disposed on the left side of FIG. 1, has pressure exerted thereon by a spring 48 of the support leg 38, and contributes to the drive or rotation of the drum 10, only to the extent of the force exerted by the spring 42. However, in order for the mechanism to operate equally well in both rotational directions, it is, in general, desirable to use a single energizing wheel 20, with two rotors 32 on each side thereof.

If necessary, a plurality of drive means 18 can be used arranged serially and aligned with an appropriate drum.

Having thus described the invention, what I claim as new and desire to be secured by Letters Patent, is as follows:

1. A drive mechanism, for use in rotating a relatively large drum rotatable about a substantially horizontal axis of rotation,
   comprising in combination:
   spring-support means, said drum being supported rotatably from said spring-support means, and
   drive means including an energizable rotor, first guide means resiliently and rotatably supporting said energizable motor from said spring-support means, said motor being in operative frictional contact with the circumference of said drum, for rotating said drum when energized, an energizing wheel in frictional driving connection with said energizable rotor for energizing it to revolve in a predetermined rotational direction, so as to drive said drum in a rotational direction opposite to said predetermined rotational direction, and second guide means rotatably supporting said energizing wheel from said spring-support means.

2. A drive mechanism according to claim 1, said drive means further comprising a second energizable rotor resiliently and rotatably supported on said support about an axis of rotation located on the other side of a plane passing through the axes of rotation of said drum and the first energizing wheel, and in frictional contact with the circumference of said drum.

3. A drive mechanism according to claim 1, wherein the energizable rotor includes a first shaft, and said energizing wheel includes a second shaft, and said first guide means includes a first elongated guide pivotably supported with one end thereof on said first shaft, and said second guide means includes a second elongated guide pivotably supported with one end thereof on said second shaft, the other ends of said guides being pivotably connected to one another, and resilient means supporting a portion of said second guide at a position spaced apart from said second shaft, thereby pressing the energizable rotor into frictional contact with said drum circumference and with said energizing wheel.

4. A drive mechanism according to claim 3, wherein said guides form an acute angle with one another.

5. A drive mechanism according to claim 1, wherein said rotor includes rollers.

6. A drive mechanism according to claim 5, wherein said energizable rotor includes a plurality of hubs of prearranged hub diameters, a friction ring of yieldably resilient material, and of a predetermined ring diameter disposed on each hub, and at least one spacer of a predetermined diameter separating two adjacent hubs from one another, said predetermined diameter being larger than said hub diameter, but less than said ring diameter.

7. A drive mechanism according to claim 5, wherein each friction ring is convergently tapered in a radially outward direction.

8. A drive mechanism according to claim 1, wherein said rotor has a predetermined width, and said drum has a circumference zone of increased external diameter in the region of the rotor width, whereby the rotor will be in frictional contact with the drum circumference at said zone.

9. A drive mechanism, as claimed in claim 1, further comprising resilient means urging said rotor into frictional rolling contact with both said energizing wheel and said drum circumference.

10. A drive mechanism, as claimed in claim 1, said rotor and said energizing wheel each being formed as a roll.

11. A drive mechanism according to claim 8, wherein said drum has a zone of increased wall thickness in the region of said rotor width.

* * * * *